(12) United States Patent
Wallace et al.

(10) Patent No.: US 9,314,326 B2
(45) Date of Patent: Apr. 19, 2016

(54) SYSTEM AND METHOD FOR RETAINING VASO-OCCLUSIVE DEVICES WITHIN AN ANEURYSM

(75) Inventors: Michael Wallace, Fremont, CA (US); Joseph Eder, Los Altos, CA (US); Brent C. Gerberding, Alameda, CA (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 973 days.

(21) Appl. No.: 13/091,608

(22) Filed: Apr. 21, 2011

(65) Prior Publication Data
US 2011/0196413 A1 Aug. 11, 2011

Related U.S. Application Data

(63) Continuation of application No. 11/617,293, filed on Dec. 28, 2006, now abandoned, which is a continuation of application No. 10/121,980, filed on Apr. 12, 2002, now abandoned.

(51) Int. Cl.
*A61F 2/06* (2013.01)
*A61B 17/12* (2006.01)

(52) U.S. Cl.
CPC ............ *A61F 2/06* (2013.01); *A61B 17/12022* (2013.01); *A61B 17/12113* (2013.01); *A61B 17/12172* (2013.01); *A61B 2017/12063* (2013.01)

(58) Field of Classification Search
CPC .................... A61B 17/12109; A61B 17/12113
USPC .......... 606/200, 191, 194, 108, 151, 157–158
See application file for complete search history.

(56) References Cited

U.S. PATENT DOCUMENTS

| 4,739,768 | A | | 4/1988 | Engelson |
| 4,830,003 | A | | 5/1989 | Wolff et al. |
| 4,991,602 | A | | 2/1991 | Amplatz et al. |
| 4,994,069 | A | | 2/1991 | Ritchart et al. |
| 5,122,136 | A | | 6/1992 | Guglielmi et al. |
| 5,250,071 | A | | 10/1993 | Palermo |
| 5,261,916 | A | | 11/1993 | Engelson |
| 5,354,295 | A | | 10/1994 | Guglielmi et al. |
| 5,527,338 | A | * | 6/1996 | Purdy .......................... 606/200 |
| 5,725,552 | A | | 3/1998 | Kotula et al. |

(Continued)

FOREIGN PATENT DOCUMENTS

| WO | WO 99/05977 | 12/1999 |
| WO | WO 00/13593 | 3/2000 |

*Primary Examiner* — Mary Hoffman
(74) *Attorney, Agent, or Firm* — Vista IP Law Group, LLP

(57) ABSTRACT

The present invention is directed to systems for occluding an aneurysm having an aneurysmal neck and an aneurysmal inner wall. Generally, a device in accordance with the present invention includes a mesh-like structure that is integrally composed of a shape-memory alloy such as NiTi. The device is deployed within the aneurysm through the aneurysmal neck. The device is configured to be in a deployed state and an undeployed state, and is configured to transition from the undeployed state to the deployed state by exposure to a higher temperature and/or by being unconstrained. The device may function to retain finer vaso-occlusive devices such as vaso-occlusive coils and/or embolic liquids. Furthermore, the device itself may function as a vaso-occlusive device.

12 Claims, 8 Drawing Sheets

(56) References Cited

U.S. PATENT DOCUMENTS

| | | |
|---|---|---|
| 5,928,260 A | 7/1999 | Chin et al. |
| 5,944,730 A * | 8/1999 | Nobles et al. ............... 606/151 |
| 5,944,738 A * | 8/1999 | Amplatz et al. ............. 606/213 |
| 5,944,750 A | 8/1999 | Tanner et al. |
| 5,951,599 A | 9/1999 | McCrory |
| 6,063,070 A | 5/2000 | Eder |
| 6,077,281 A | 6/2000 | Das |
| 6,080,182 A | 6/2000 | Shaw et al. |
| 6,086,577 A | 7/2000 | Ken et al. |
| 6,093,199 A | 7/2000 | Brown et al. |
| 6,168,615 B1 | 1/2001 | Ken et al. |
| 6,168,622 B1 | 1/2001 | Mazzocchi |
| 6,299,619 B1 | 10/2001 | Greene, Jr. et al. |
| 6,344,048 B1 | 2/2002 | Chin et al. |
| 6,346,117 B1 | 2/2002 | Greenhalgh |
| 6,368,339 B1 | 4/2002 | Amplatz |
| 6,375,668 B1 | 4/2002 | Gifford et al. |
| 6,383,174 B1 | 5/2002 | Eder |
| 6,391,037 B1 | 5/2002 | Greenhalgh |
| 6,447,531 B1 | 9/2002 | Amplatz |
| 6,454,780 B1 | 9/2002 | Wallace |
| 6,506,204 B2 | 1/2003 | Mazzocchi |
| 6,511,468 B1 | 1/2003 | Cragg et al. |
| 6,551,303 B1 * | 4/2003 | Van Tassel et al. .......... 604/508 |
| 6,579,303 B2 | 6/2003 | Amplatz |
| 6,585,748 B1 | 7/2003 | Jeffree |
| 6,599,308 B2 | 7/2003 | Amplatz |
| 6,605,102 B1 * | 8/2003 | Mazzocchi et al. .......... 606/200 |
| 6,613,074 B1 | 9/2003 | Mitelberg et al. |
| 6,638,257 B2 | 10/2003 | Amplatz |
| 6,682,546 B2 | 1/2004 | Amplatz |
| 6,746,468 B1 | 6/2004 | Sepetka et al. |
| 6,811,560 B2 | 11/2004 | Jones et al. |
| 7,128,736 B1 | 10/2006 | Abrams et al. |
| 7,326,225 B2 | 2/2008 | Ferrera et al. |
| 7,331,980 B2 | 2/2008 | Dubrul et al. |
| 8,034,061 B2 | 10/2011 | Amplatz et al. |
| 8,142,456 B2 | 3/2012 | Rosqueta et al. |
| 8,313,505 B2 | 11/2012 | Amplatz et al. |
| 8,323,309 B2 * | 12/2012 | Khairkhahan et al. ........ 606/200 |
| 8,357,180 B2 * | 1/2013 | Feller et al. .................... 606/213 |
| 8,361,104 B2 | 1/2013 | Jones et al. |
| 8,361,138 B2 | 1/2013 | Adams |
| 8,398,670 B2 | 3/2013 | Amplatz et al. |
| 8,444,668 B2 | 5/2013 | Jones et al. |
| 8,454,633 B2 | 6/2013 | Amplatz et al. |
| 8,758,389 B2 | 6/2014 | Glimsdale |
| 8,764,787 B2 * | 7/2014 | Ren ............................ 606/200 |
| 8,777,974 B2 | 7/2014 | Amplatz et al. |
| 8,790,363 B2 | 7/2014 | Ferrera et al. |
| 8,821,529 B2 | 9/2014 | Kariniemi et al. |
| 8,864,790 B2 | 10/2014 | Strauss et al. |
| 8,906,057 B2 * | 12/2014 | Connor et al. ................ 606/200 |
| 8,919,389 B2 | 12/2014 | Gries |
| 8,940,015 B2 | 1/2015 | Kariniemi |
| 8,961,556 B2 | 2/2015 | Amplatz et al. |
| 9,039,726 B2 | 5/2015 | Becking |
| 2006/0247680 A1 | 11/2006 | Amplatz et al. |
| 2009/0112251 A1 | 4/2009 | Qian et al. |
| 2010/0023046 A1 | 1/2010 | Heidner et al. |
| 2010/0106235 A1 | 4/2010 | Kariniemi et al. |
| 2011/0144669 A1 | 6/2011 | Becking et al. |
| 2013/0012979 A1 | 1/2013 | Amplatz et al. |
| 2013/0204289 A1 | 8/2013 | Dasnurkar et al. |
| 2013/0253572 A1 | 9/2013 | Molaei et al. |
| 2014/0135810 A1 | 5/2014 | Divino et al. |
| 2014/0135828 A1 | 5/2014 | Amplatz et al. |
| 2014/0214077 A1 | 7/2014 | Glimsdale |
| 2014/0257357 A1 | 9/2014 | Ren |
| 2014/0257361 A1 | 9/2014 | Prom |
| 2014/0288591 A1 | 9/2014 | Amplatz et al. |
| 2015/0133994 A1 | 5/2015 | Amplatz et al. |

\* cited by examiner

SYSTEM AND METHOD FOR RETAINING VASO-OCCLUSIVE DEVICES WITHIN AN ANEURYSM

RELATED APPLICATION DATA

The present application is a continuation of pending U.S. patent application Ser. No. 11/617,293, filed Dec. 28, 2006, which is a continuation of U.S. patent application Ser. No. 10/121,980 filed Apr. 12, 2002, now abandoned, the priority of which is claimed under 35 U.S.C. §120, and the contents of which is incorporated herein by reference in their entirety, as though set forth in full.

FIELD OF THE INVENTION

The present invention relates generally to vaso-occlusion, and more particularly to systems and methods for retaining vaso-occlusive devices within an aneurysm.

BACKGROUND OF THE INVENTION

Different implantable medical devices have been developed for treating a number of ailments associated with body lumens. In particular, occlusive devices are useful in filling vascular or other body spaces. Some body spaces, such as vascular aneurysms, are formed due to a weakening in the wall of an artery. Often these aneurysms are the site of internal bleeding and stroke. A variety of different embolic agents are known to be, at least arguably, suitable for treatment of these anomalies. These treatments are commonly known as "artificial vaso-occlusion."

Over the past few years, advancements in the artificial occlusion of vessels and aneurysms have included the delivery and implantation of metal coils as vaso-occlusive devices. Implantable metal coils that are useful as artificial occlusion devices in vasculature lumens or aneurysms are herein referred to as "vaso-occlusive coils." Vaso-occlusive coils are generally constructed of a wire, usually made of a metal or metal alloy that is wound to a helix. The vaso-occlusive coil assumes an irregular shape upon discharge of the device from the distal end of the catheter. A variety of vaso-occlusive coils are known. For instance, U.S. Pat. No. 4,994,069, issued to Ritchart et al., shows a flexible, preferably coiled, wire for use in small vessel vaso-occlusion. Unlike vaso-occlusive coils used prior to that time, Ritchart et al. teach a coil that is fairly soft and is delivered to the site using a pusher within a catheter lumen. Upon discharge from the delivery catheter, the coil may undertake any number of random or regular configurations used to fill the site.

The coils may be used for small vessel sites, e.g., 0.5-6 mm in diameter. The coils themselves are described as being between 0.010 and 0.030 inches in diameter. The length of the coil wire is typically 15 to 20 times the diameter of the vessel to be occluded. The wire used to make up the coils may be, for instance, 0.002 to 0.006 inches in diameter. Tungsten, platinum, and gold threads or wires are said to be preferred. These coils have a variety of benefits including the fact that they are relatively permanent, they may be easily imaged radiographically, they may be located at a well defined vessel site, and they can be retrieved.

In addition to the various types of space filling mechanisms and geometries of vaso-occlusive coils, other particularized features of coil designs, such as mechanisms for delivering vaso-occlusive coils through delivery catheters and implanting them in a desired occlusion site, have also been described. The examples of categories of vaso-occlusive coils based upon their delivery mechanisms include pushable coils, mechanically detachable coils, and electrolytically detachable coils.

One example of the type of vaso-occlusive coil referred to above as the "pushable coil" is disclosed in Ritchart et al., discussed above. Pushable coils are commonly provided in a cartridge and are pushed or "plunged" from the cartridge into a delivery catheter lumen. A pusher advances the pushable coil through and out of the delivery catheter lumen and into the site for occlusion.

Mechanically detachable vaso-occlusive coils are typically integrated with a pusher rod and are mechanically detached from the distal end of that pusher after exiting a delivery catheter. Examples of such mechanically detachable vaso-occlusive coils are found in U.S. Pat. No. 5,261,916 to Engelson or U.S. Pat. No. 5,250,071 to Palermo.

Finally, examples of electrolytically detachable vaso-occlusive coils may be found in U.S. Pat. Nos. 5,122,136 and 5,354,295, each issued to Guglielmi et al. In these devices, the vaso-occlusive portion of the assembly is attached to a pusher via a small, electrolytically severable joint. The electrolytically severable joint is severed by the placement of an appropriate voltage on the core wire. The joint erodes in preference either to the vaso-occlusive coil itself or to the pusher core wire.

As noted above, aneurysms present a particularly acute medical risk due to the dangers of potential rupture of the thin wall inherent in such aneurysms. Occlusion of aneurysms by use of vaso-occlusive coils without occluding the adjacent artery is a special challenge and is a desirable method of reducing such risk of rupture. These vaso-occlusive devices are typically placed in an aneurysm in a manner described in U.S. Pat. No. 4,739,768 issued to Engelson. In particular, a microcatheter is initially steered into or adjacent to the entrance of an aneurysm, typically aided by the use of a steerable guidewire. The wire is then withdrawn from the microcatheter lumen and replaced by the vaso-occlusive coil. The vaso-occlusive coil is advanced through and out of the microcatheter, desirably being completely delivered into the aneurysm.

However, after, or perhaps during, delivery of the coil into the aneurysm, there is a specific risk that a portion of the coil might migrate out of the aneurysm entrance zone and into the feeding vessel. The presence of the coil in that feeding vessel may cause a highly undesirable occlusion there. Also, there is a quantifiable risk that the blood flow in the vessel and aneurysm may induce movement of the coil farther out of the aneurysm, resulting in a more developed embolus in the feeding vessel.

One type of aneurysm, commonly known as a "wide neck aneurysm," is known to present particular difficulty in the placement and retention of vaso-occlusive coils, because vaso-occlusive coils lacking substantial secondary shape strength may be difficult to maintain in position within an aneurysm no matter how skillfully they are placed. Wide neck aneurysms are herein referred to as aneurysms of vessel walls having a neck or "entrance zone" from the adjacent vessel, wherein the entrance zone has a diameter that either: (1) is at least 80% of the largest diameter of the aneurysm; or (2) is clinically observed to be too wide effectively to retain vaso-occlusive coils that are deployed using the techniques discussed above.

One approach to occlude such an aneurysm is described in U.S. Pat. No. 6,168,622, which describes a vaso-occlusive device with a secondary shape having a bulbous body portion and an anchor. The bulbous body portion is deployed within the aneurysm while the anchor is set just outside of the aneurysm, covering the aneurysm's neck or entrance zone. The device is integrally formed from a tube—clamped at both ends—of braided Nickel-Titanium (NiTi) wires. The bulbous body functions to occlude the aneurysm, while the anchor covers the entrance zone. In some cases, it may still be desirable to deploy vaso-occlusive coils with such a device, but the bulbous body of the vaso-occlusive device does not provide much space within the aneurysm to allow for insertion and deployment of the coils.

Accordingly, an improved system and method for occluding an aneurysm neck would be desirable.

SUMMARY OF INVENTION

The present invention is directed to systems and methods for occluding an aneurysm having an aneurysmal neck and an aneurysmal inner wall. Generally, a device in accordance with the present invention includes a mesh-like structure that may be integrally composed of a shape-memory alloy such as NiTi. The device may be deployed within the aneurysm through the aneurysmal neck. The device may be configured to be in a deployed state and an undeployed state, and may be configured to transition from the undeployed state to the deployed state by exposure to a higher temperature and/or by being released from a compressive force. The device may function to retain finer vaso-occlusive devices such as vaso-occlusive coils and/or embolic liquids. Furthermore, the device itself may function as a vaso-occlusive device. The device may be delivered to the aneurysm by, e.g., a catheter.

In accordance with a first aspect of the present invention, at least one of the proximal and distal ends of the mesh-like structure is configured to be inserted through the aneurysmal neck when in an undeployed state, and configured to flare open and expand against at least a portion of the aneurysmal inner wall when in a deployed state. Having a flared open end may advantageously allow the device to conform to the shape of the aneurysm.

In accordance with another aspect of the present invention, the distal end of the mesh-like structure may be configured to be inserted through the aneurysmal neck when in an undeployed state and configured to expand into a retainer against at least a portion of the aneurysmal inner wall when in a deployed state. The proximal end may be configured to expand into an anchor just outside of the aneurysm to secure the mesh-like structure in position.

Other objects and features of the present invention will become apparent from consideration of the following description taken in conjunction with the accompanying drawings.

BRIEF DESCRIPTION OF THE DRAWINGS

In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENT

Figure 1:
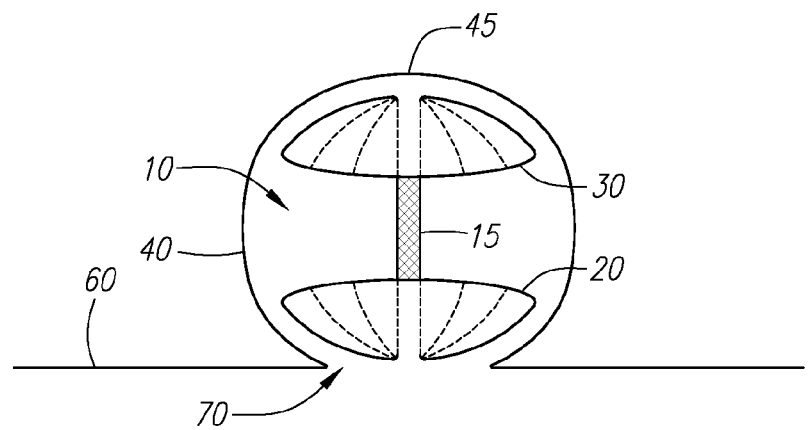
FIG. 1 is an illustration of a vaso-occlusive device constructed in accordance with a preferred embodiment of the present inventions, wherein the vaso-occlusive device is shown fully deployed within an aneurysm.

Turning to FIG. 1, a vaso-occlusive element 10 constructed in accordance with a preferred embodiment of the present invention is shown completely deployed within an aneurysm 40 of a blood vessel 60. The aneurysm 40 is shown with an oppositely disposed neck 70 and dome 45. When deployed in its secondary shape, i.e., its deployed shape, the vaso-occlusive element 10 generally includes a central tubular element 15 and proximal 20 and distal 30 ends that are flared open into "umbrella" shapes. As illustrated, the flared opened ends 20/30 advantageously conform to the shape of the aneurysm 40. The diameter of the proximal end 20 of the vaso-occlusive element 10 is larger than the neck 70, and thus the proximal end 20 may completely cover the neck 70.

As will be described in further detail below, the vaso-occlusive element 10 is manufactured from a relatively dense braid. In this manner, the proximal end 20 may densely cover the neck 70 and function as a retainer. Thus, finer vaso-occlusive devices, such as vaso-occlusive coils or embolic liquids, may effectively be retained within the aneurysm 40, or at the least, the likelihood of these devices migrating out from the aneurysm 40 is minimized. Further, as can be appreciated by one of ordinary skill in the art, the relatively dense coverage of the proximal end 20 allows the vaso-occlusive element 10 itself to function as a vaso-occlusive device. The flared open distal end 30 is placed adjacent the dome 45 of the aneurysm 40 and allows the element 10 to safely conform to the shape of the dome 45. This allows for the distal end 30 to function as an anchor and secure itself within the aneurysm 40 without the need to conform to the entire shape of the aneurysm 40. Thus, the element 10 may conform to a large variety of shapes and sizes of aneurysms 40 since the element 10 need only be secured within the aneurysm 40 by conforming the flared open distal end 30 to the dome 45.

Figure 2A:
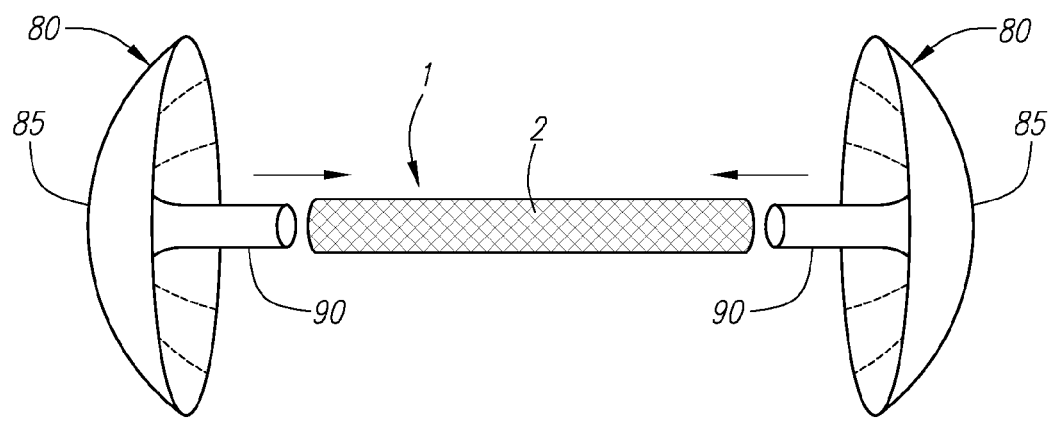
FIGS. 2(a) and 2(b) illustrate one preferred method of manufacturing the vaso-occlusive device of FIG. 1 in accordance with the present inventions.
Figure 2B:
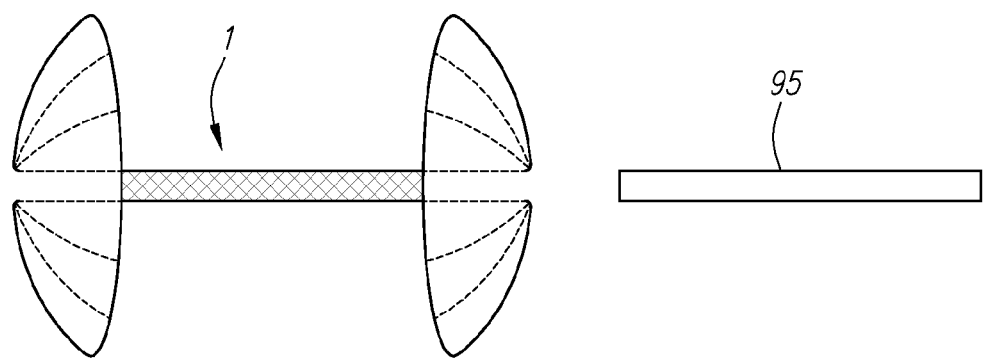

Turning to FIGS. 2(a)-(b), one preferred method of manufacturing the vaso-occlusive device 10 will now be described. First, a braided tubular element 1 is constructed by braiding multiple fine wires 2 together. The tubular element 1 may also be formed of wires with varying diameters braided together. It may be desirable to use a larger number of wires 2 when forming the tubular element 1, resulting in a relatively dense braid, which provides denser coverage within the aneurysm 40. Optionally, the tubular element 1 may be radiopaque. One method involves braiding a radiopaque fiber, such as platinum, Pt, or gold, Au, into the tubular element 1. Another method involves plating or coating the tubular element 1 with radiopaque material. Additionally, one or more radiopaque markers may be added to the tubular element 1.

Preferably, the wires 2 are made from a shape memory alloy, which can be of any type, but preferably is a "one way" trainable shape memory alloy. A preferable shape memory alloy for forming the braided tubular element 1 is Nickel-Titanium (NiTi)—e.g., 144 strands of 0.001" NiTi wires. Shape memory alloys comprise a unique class of metal alloys that, once trained, are configured to "remember" a preselected shape, i.e., deployed shape, and can return to the preselected shape even if subsequently reshaped. To be trained to "remember" a first preselected shape, the shape memory alloy is molded and heated at or above a training, or austenite, temperature to place the shape memory alloy in an austenite phase. In the austenite phase, the shape memory alloy is formed in the first preselected shape and then, once formed, is permitted to cool to a martensite finish temperature, whereupon the shape memory alloy enters a martensite phase. The martensite finish temperature can be any temperature that is less than the training temperature. Upon entering the martensite phase, the shape memory alloy has been trained to "remember" the first preselected shape. While in the martensite phase, the alloy is in a soft state and is formed into a second preselected shape, e.g., an undeployed shape. The shape memory alloy in the martensite phase is configured to maintain the second preselected shape and, if subsequently reheated to an activation temperature, automatically returns to the first preselected shape. The activation temperature can comprise any temperature that is greater than the martensite finish temperature and generally approximately equals the training temperature. Once the first preselected shape has been recovered, the shape memory alloy is configured to maintain the first preselected shape irrespective of temperature. Generally, as can be appreciated by one of ordinary skill in the art, the training, martensite finishing, and activation temperatures for a shape memory alloy are adjustable, depending on the composition. For example, a slight extra amount of Nickel added to a NiTi alloy composition can change the training temperature from 0.degree. C. to 100.degree. C.

Generally, the vaso-occlusive device 10 described above is delivered to the aneurysm 40 via a delivery catheter. The catheter delivers the device 10 to the aneurysm 40 and during the delivery, the device 10 maintains an undeployed shape, e.g., the original tubular shape—methods of delivery will be described in more detail below. When the device 10 is deployed, the device 10 expands into its deployed shape, e.g., having flared open proximal and distal ends 20/30, as shown in FIG. 1. Using a shape memory alloy to form the device 10 provides for alternative methods of expanding the device 10 into its deployed shape within the aneurysm 40.

One method involves configuring the device 10 to self-expand within the aneurysm 40 when deployed and exposed to the temperature of the aneurysm 40. To configure the device 10 to self-expand within the aneurysm 40 when deployed and exposed to the temperature of the aneurysm 40, the training and activation temperatures are adjusted to be at, or just below, the temperature of the aneurysm, which is approximately 37.degree. Celsius—the human body temperature. The martensite temperature is adjusted to be at a lower temperature. With these temperatures set, the device 10 is heated to, or above the training temperature—austenite phase—and shaped into its desired deployed shape, as described above. Then, the temperature is lowered to, or below, the martensite finish temperature—martensite phase—and shaped into its desired undeployed shape. Subsequently, the device 10 is then placed inside the catheter as will be described below. The catheter can be constructed of a material that insulates the device 10 from the outside environment and maintains the temperature of the device 10 below the activation temperature. Thus, when the catheter is inserted into the lumen 75 of the blood vessel 60, the device 10 does not expand into its deployed shape within the catheter. When the device 10 is deployed into the aneurysm 40 and exposed to the aneurysm temperature, the temperature of the device will rise at or above the activation temperature, and the device 10 will expand into its deployed shape. Because the alloy is preferably "one way" trained, the device 10 will then be configured to maintain the deployed shape irrespective of the temperature, as described above.

An alternative method for expanding the device 10 into its deployed shape within the aneurysm utilizes the super-elastic characteristic of shape memory alloys. After the device 10 is configured to maintain its deployed shape irrespective of the temperature, as described above, the device 10 is then maintained in its austenite phase. When the device 10 is in its austenite phase, the device 10 is super-elastic, i.e., the device 10 may be deformed to a certain degree and still be able to return to its deployed shape. The device 10 is then placed within the catheter as will be described below, with the inner wall of the catheter compressing the device 10 into its undeployed shape. When the device 10 is released out of the catheter into the aneurysm 40, the uncompressed device 10 automatically expands into its deployed shape because of its super-elasticity.

Further details on the structure and manufacturing process of braided tubular elements 1 are disclosed in U.S. Pat. No. 6,168,622 issued to Mazzochhi, column 4, line 33 to column 6, line 24, and FIGS. 1A and 1B, of which are hereby incorporated by reference.

Forming the deployed shape shown in FIG. 1 is achieved by using two mandrels 85, each having a cylindrical portion 90 and an umbrella dome-shaped mold 85, as illustrated in FIG. 2(a). To flare open the ends of the element 1, each end is placed over the cylindrical portion 90 of a mandrel 85 and compressed against the dome 85, causing the ends to conform to the shape of the dome 85 and flare open. The assembly of the two mandrels 80 and the element 1 is then heated at or above the training temperature to place the element 1 in the austenite phase. The assembly is maintained at that temperature until the deployed shape has been formed.

Then, the assembly is cooled to, or below, the martensite finishing temperature to place the element 1 in the martensite phase. In the martensite phase, the mandrels 80 are removed from the element 1, and the element 1 is formed into an undeployed shape, e.g., the original tubular shape. This may be achieved by placing the element 1 over a cylindrical mandrel 95 and compressing the flared ends to conform to the shape of the cylindrical mandrel 95, as shown in FIG. 2b. Subsequently, the element 1 may be reheated to the activation temperature, causing the element 1 to return to the deployed shape. Once the deployed shape has been recovered, the element 1 is configured to maintain the deployed shape irrespective of temperature.

Figure 3:
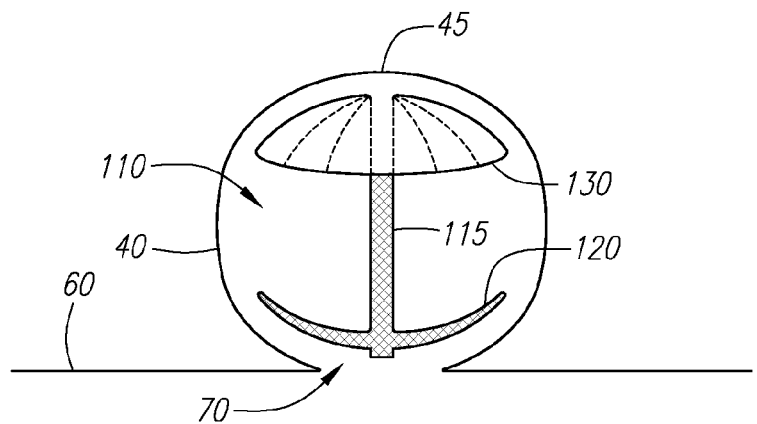
FIG. 3 is an illustration of another vaso-occlusive device constructed in accordance with a preferred embodiment of the present inventions, wherein the vaso-occlusive device is shown fully deployed within an aneurysm.

Turning to FIG. 3, another vaso-occlusive element 110 constructed in accordance with a preferred embodiment of the present invention is shown completely deployed within the aneurysm 40. As with the embodiment in FIG. 1, the vaso-occlusive element 110, when deployed, generally includes a central tubular element 115 and a flared distal end 130. The vaso-occlusive element 110 further includes a proximal end 120 shaped as a flattened disk, which functions as a retainer. The proximal end 130 has a diameter larger than the diameter of the neck 70, and thus completely covers the entrance zone 150. The flattened disk 130 has a layer of braided wires on both sides, and thus may advantageously provide two layers of braided wires to cover the entrance zone 150 instead of one layer with the flared open proximal end 20 shown in FIG. 1. As with the flared open distal end 30 of the vaso-occlusive element 10, shown in FIG. 1, the flared open distal end 130 is placed adjacent the dome 45 of the aneurysm 40 and allows the element 110 to safely conform to the shape of the dome 45.

Figure 4:
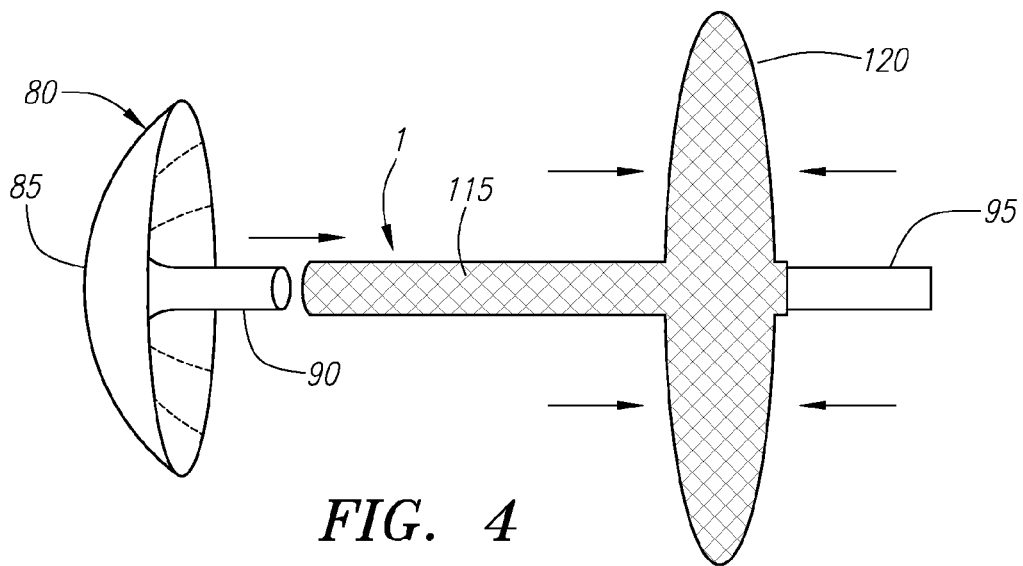
FIG. 4 illustrates one preferred method of manufacturing the vaso-occlusive device of FIG. 3 in accordance with the present inventions.

Turning to FIG. 4, one preferred method of manufacturing the vaso-occlusive device 110 shown in FIG. 3 will now be described. As described above, a braided tubular element 1 is first constructed. Forming the deployed shape is achieved by using one of the mandrels 85 shown in FIG. 2(a) and the cylindrical mandrel shown in FIG. 2(b), as illustrated in FIG. 4. As described above, to flare open the distal end of the element 1, the distal end is placed over the cylindrical portion 90 of the mandrel 85 with the dome 80 and compressed against the dome 80, causing the distal end to flare open. To form the flattened disk 120, the proximal end is placed on the cylindrical mandrel 95. The proximal tip and a portion of the central tubular portion 115 are then compressed together along the axis of the cylindrical mandrel 95. This causes the proximal end to expand into a flattened disk 120.

The assembly of the two mandrels 80/95 and the element 1 is then heated at or above the training temperature to place the element 1 in the austenite phase. The assembly is maintained at that temperature until the deployed shape 110 has been formed. Then, the assembly is cooled to, or below, the martensite finishing temperature to place the element 110 in the martensite phase. In the martensite phase, the mandrels 80/95 are removed from the element 110, and the element 110 is formed into an undeployed shape, e.g., the original tubular shape 1. This is achieved by placing the element 110 over the cylindrical mandrel 95 and compressing the flared open end and flattened disk to conform to the shape of the cylindrical mandrel 95, as shown in FIG. 2(b). If the element 1 is configured to expand into its deployed shape upon exposure to a higher temperature, then the element 1 may be placed within a delivery catheter in preparation for deployment, as described above. Alternatively, if the element 110 is configured to expand upon being released by a compressive force, then the element 1 is reheated to, or above, the activation temperature, causing the element 1 to return to the deployed shape 110 and to be configured to maintain the deployed shape 110 irrespective of temperature.

Figure 5:
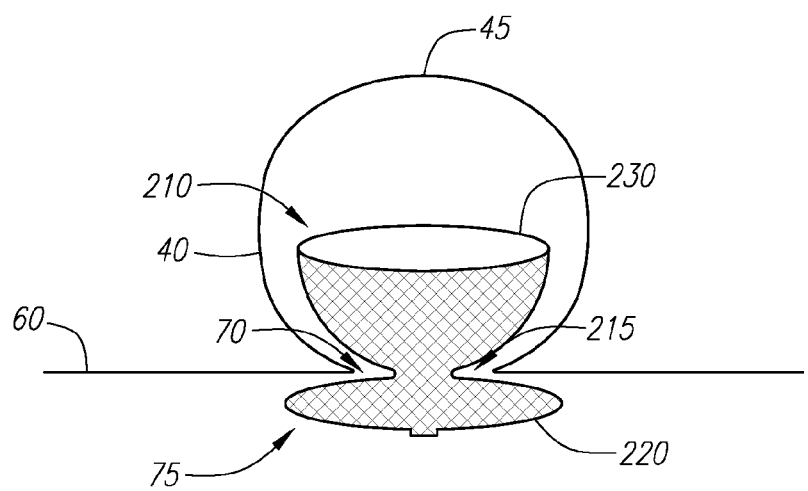
FIG. 5 is an illustration of still another vaso-occlusive device constructed in accordance with a preferred embodiment of the present inventions, wherein the vaso-occlusive device is shown fully deployed within an aneurysm.

Turning to FIG. 5, another vaso-occlusive element 210 constructed in accordance with a preferred embodiment of the present invention is shown deployed within the aneurysm 40. When in a deployed shape, the element 210 generally includes a central portion 215 and a distal end flared open into a "cup" shape 230. Alternatively, the distal end may be flared open into a "cone" shape. The vaso-occlusive element 210 further includes a proximal end 220 shaped as a flattened disk. The proximal end 220 has a diameter larger than the diameter of the neck 70. Only the flared open cup shape 230 is deployed within the aneurysm 40, whereas the flattened disk 220 is deployed in the lumen 75 of the blood vessel 60 just outside of the aneurysm 40, functioning as an anchor for the element 210. The cup shaped distal end 230 may retain fine vaso-occlusive devices such as vaso-occlusive coils and embolic liquids.

Figure 6:
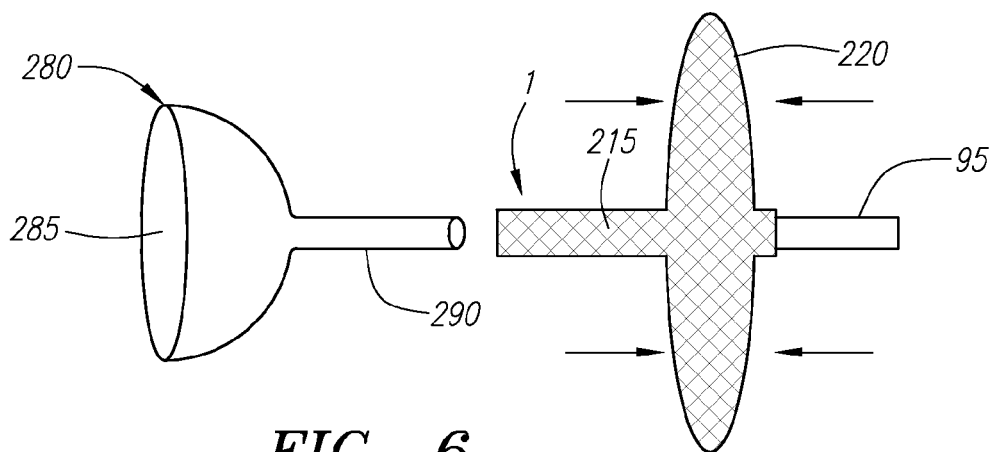
FIG. 6 illustrates one preferred method of manufacturing the vaso-occlusive device of FIG. 5 in accordance with the present inventions.

Turning to FIG. 6, one preferred method of manufacturing the vaso-occlusive device 310 shown in FIG. 5 will now be described. As described above, a braided tubular element 1 is first constructed. Forming the deployed shape is achieved by using a mandrel 280 having a cup shaped dome 285 facing outward coupled to a cylindrical portion 290 and a cylindrical mandrel 95. To form the cup shape, the distal end of the element 1 is placed over the cylindrical portion 290 of the mandrel 280 having the dome 285 and compressed against the dome 285, causing the distal end to flare open into a cup shape. To form the flattened disk, the proximal end is placed over the cylindrical mandrel 95. The proximal tip and a portion of the central tubular portion 215 are then compressed together along the axis of the cylindrical mandrel 95. This causes the proximal end to expand into a flattened disk 220.

The assembly of the two mandrels 280/95 and the element 1 is then heated at or above the training temperature to place the element 1 in the austenite phase. The assembly is maintained at that temperature until the deployed shape 210 has been formed. Then, the assembly is cooled to, or below, the martensite finishing temperature to place the element 210 in the martensite phase. In the martensite phase, the mandrels 280/95 are removed from the element 210, and the element 210 is formed into an undeployed shape, e.g., the original tubular shape 1. This may be achieved by placing the element 210 over the cylindrical mandrel 95 and compressing the flared open end and flattened disk to conform to the shape of the cylindrical mandrel 95. If the element 1 is configured to expand into its deployed shape upon exposure to a higher temperature, then the element 1 may be placed within a delivery catheter in preparation for deployment, as described above. Alternatively, if the element 110 is configured to expand upon being released by a compressive force, then the element 1 is reheated to, or above, the activation temperature, causing the element 1 to return to the deployed shape 110 and to be configured to maintain the deployed shape 110 irrespective of temperature.

Figure 7:
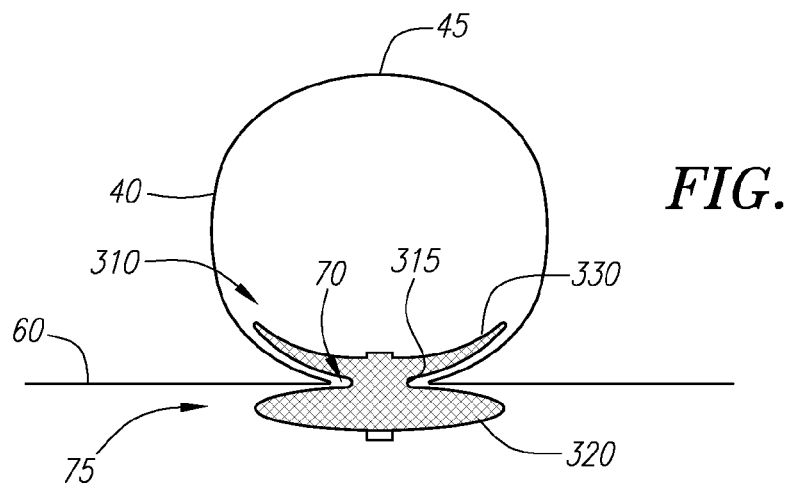
FIG. 7 is an illustration of still another vaso-occlusive device constructed in accordance with a preferred embodiment of the present inventions, wherein the vaso-occlusive device is shown fully deployed within an aneurysm.

Turning to FIG. 7, another vaso-occlusive element 310 constructed in accordance with a preferred embodiment of the present invention is shown deployed within the aneurysm 40. When in a deployed shape, the element 310 generally includes a central portion 315 and first and second flattened disks 330/320 formed at the distal and proximal ends respectively. Only the first flattened disk 330 at the distal end is deployed within the aneurysm 40 whereas the second flattened disk 320 is deployed within the lumen 75 of the blood vessel 60 just outside of the aneurysm 40, functioning as an anchor to secure the element 310 in its position. The first flattened disk 330 provides a wider coverage than the cup shape 230 shown in FIG. 5. As with the other devices described above, this device 310 may also retain fine vaso-occlusive devices such as vaso-occlusive coils and embolic liquids. The central portion 315 may be conventionally sealed to prevent the fine vaso-occlusive devices from migrating out.

Figure 8:
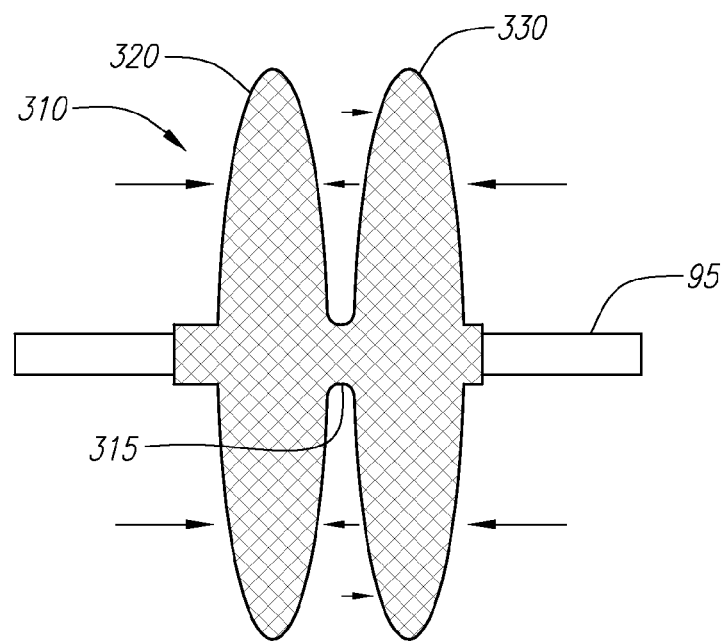
FIG. 8 illustrates one preferred method of manufacturing the vaso-occlusive device of FIG. 7 in accordance with the present inventions.

Turning to FIG. 8, one preferred method of manufacturing the vaso-occlusive device 310 shown in FIG. 7 will now be described. As described above, a braided tubular element 1 is first constructed. Forming the deployed shape is achieved by using a cylindrical mandrel 95, as illustrated in FIG. 8. To form the first flattened disk 330, the distal end is placed on the cylindrical mandrel 95. The distal tip and a portion of the central tubular portion 315 are then compressed together along the axis of the cylindrical mandrel 95. This causes the distal end to expand into a flattened disk 330. To form the second flattened disk 320, the proximal end is placed on the cylindrical mandrel 95. The proximal tip and a portion of the central tubular portion 315 are then compressed together along the axis of the cylindrical mandrel 95. This causes the proximal end to expand into a flattened disk 320.

The assembly of the mandrel 95 and the element 1 is then heated at or above the training temperature to place the element 1 in the austenite phase. The assembly is maintained at that temperature until the deployed shape 310 has been formed. Then, the assembly is cooled to, or below, the martensite finishing temperature to place the element 310 in the martensite phase. In the martensite phase, the mandrel 95 is removed from the element 310, and the element 310 is formed into an undeployed shape, e.g., the original tubular shape 1. This may be achieved by placing the element 310 over the cylindrical mandrel 95 and compressing the flattened disks 320/330 to conform to the shape of the cylindrical mandrel 95, as shown in FIG. 2(*b*). If the element 1 is configured to expand into its deployed shape upon exposure to a higher temperature, then the element 1 may be placed within a delivery catheter in preparation for deployment, as described above. Alternatively, if the element 110 is configured to expand upon being released by a compressive force, then the element 1 is reheated to, or above, the activation temperature, causing the element 1 to return to the deployed shape 110 and to be configured to maintain the deployed shape 110 irrespective of temperature.

Figure 9A:
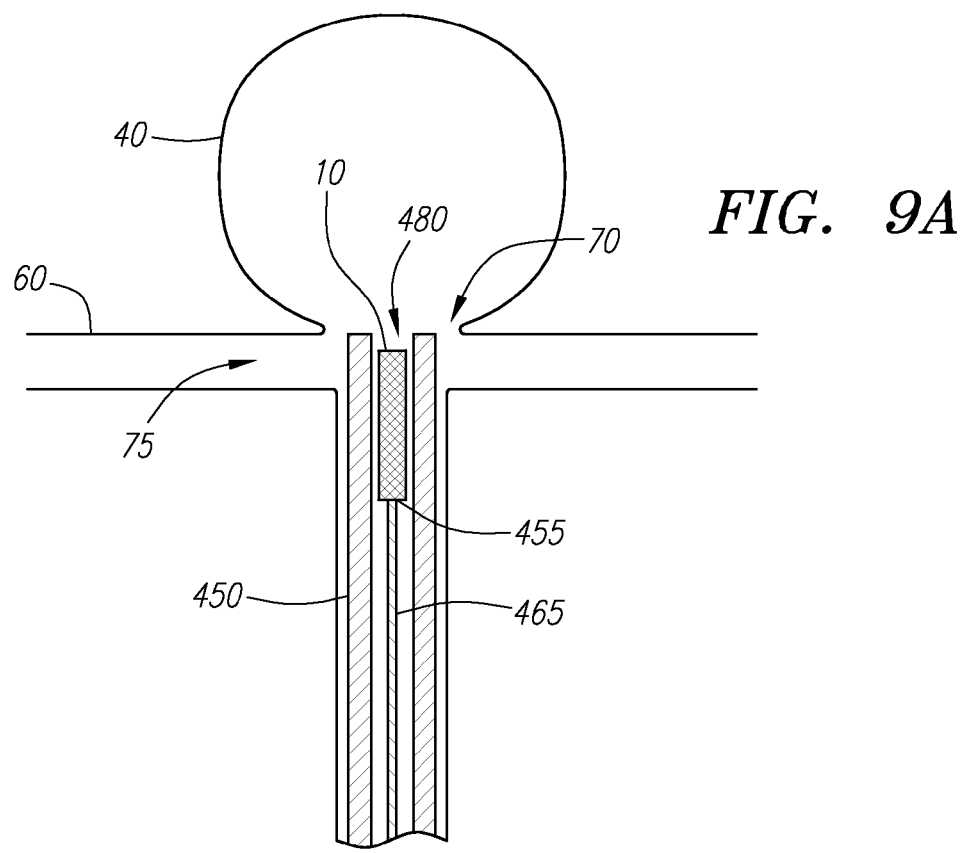
FIGS. 9(a)-(c) illustrate a preferred method of delivering and deploying the vaso-occlusive device of FIG. 1 into the aneurysm.
Figure 9B:
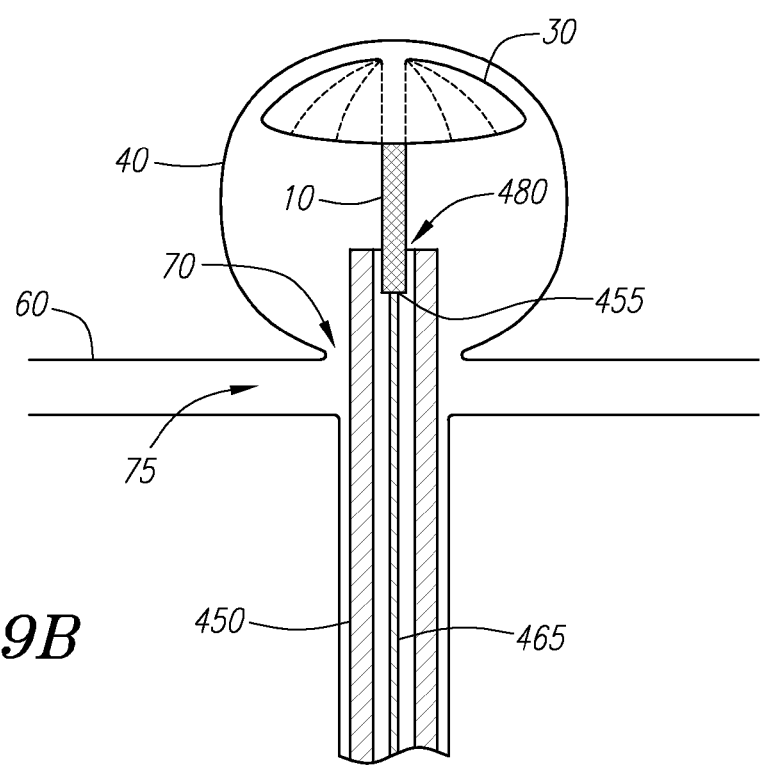
Figure 9C:
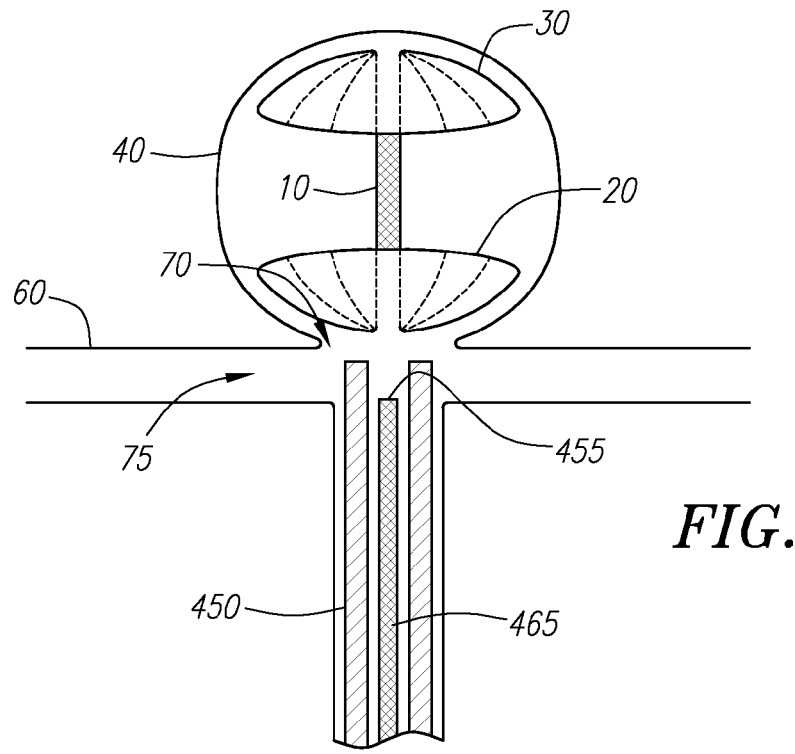
Figure 10A:
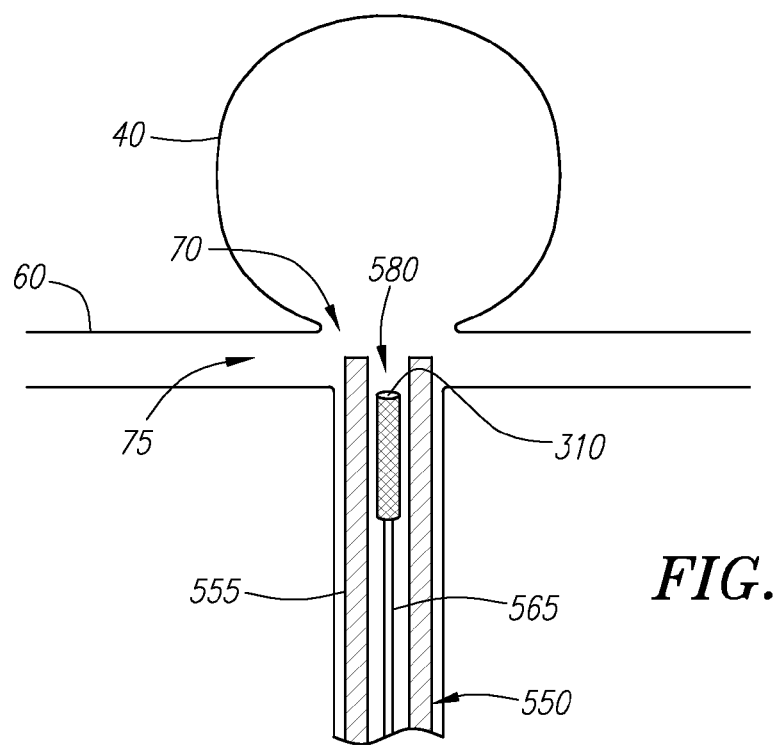
FIGS. 10(a)-(d) illustrate a preferred method of delivering and deploying the vaso-occlusive device of FIG. 7 into the aneurysm.
Figure 10B:
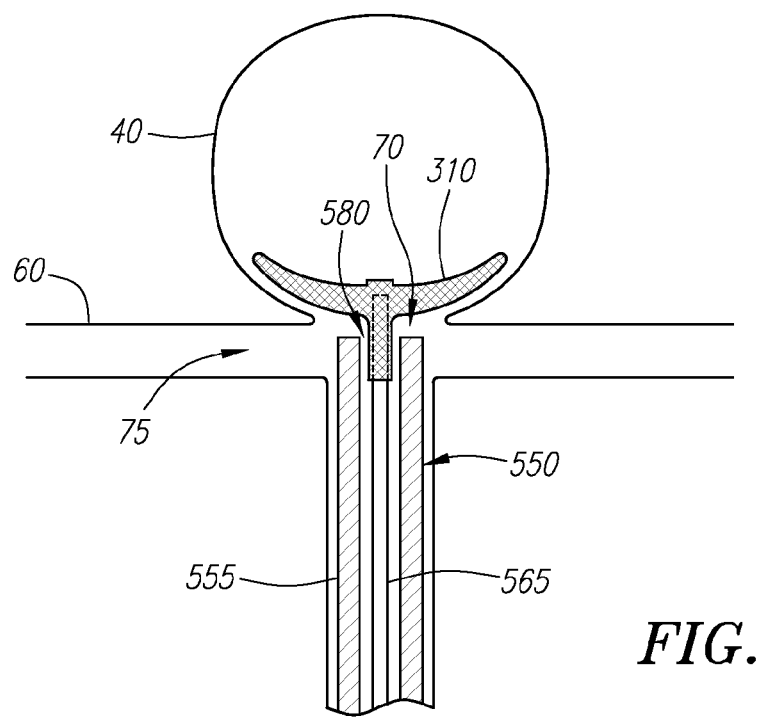
Figure 10C:
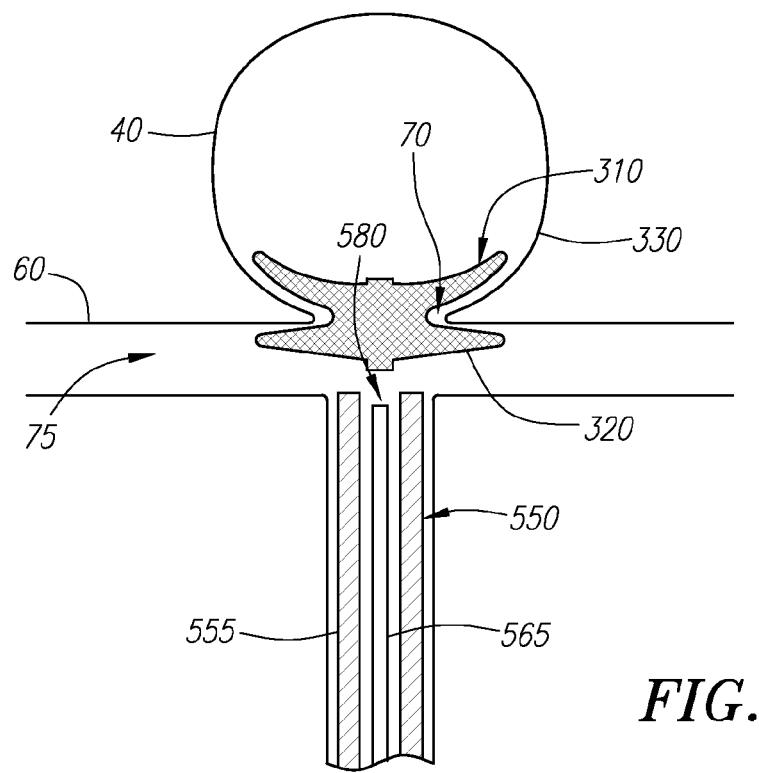
Figure 10D:
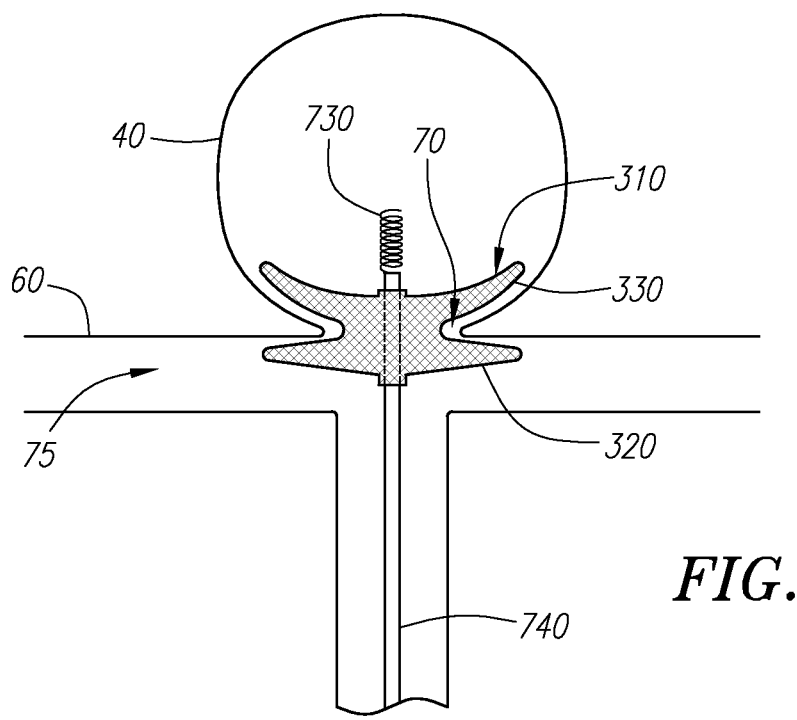

Generally, as mentioned above, the vaso-occlusive devices described above are delivered to an aneurysm within a blood vessel via a delivery catheter. Referring to FIGS. 9(*a*)-(*c*), a method of deploying a vaso-occlusive device, and in this case the vaso-occlusive device 10, to the aneurysm 40 via a delivery catheter 450 is illustrated. Turning first to FIG. 9(*a*), the catheter 450 is steered to just within the neck 70 of the aneurysm 40. At this point, the vaso-occlusive device 10 is in its undeployed shape, and is coupled to an inner guidewire 465 via an electrolytically severable joint 455. The assembly of the vaso-occlusive device 10 and the guidewire 465 extends through the lumen of the delivery catheter 450 such that the device 10 is positioned at the distal end of the catheter 450.

Turning to FIG. 9(*b*), the guidewire 465 is then pushed toward the distal end of the catheter 450 causing the vaso-occlusive device 10 to extend out of the distal end of the catheter 450, through the neck 70, and into the aneurysm 40. As the vaso-occlusive device 10 is pushed out of the catheter 450, the portion of the device 10 that is free from the constraints of the catheter 450 expands into its deployed shape, e.g., the distal end 30 flares open.

As described above, the device 10 may be configured to be in its martensite phase when delivered to the aneurysm 40 and expand upon exposure to the temperature of the aneurysm 40. Thus, when outside of the catheter 450, the temperature of the device 10 rises and the device 10 enters the austenite phase and expands into its deployed shape. Alternatively, the device 10 may be configured to be super-elastic and automatically expand upon being-unconstrained by the catheter 450.

Turning now to FIG. 9(*c*), the guidewire 465 continues to push the device 10 out of the catheter until the proximal end 20 of the device 10 is deployed within the aneurysm 40, expanding into its deployed shape, e.g., the proximal end 20 flares open, as described above with the distal end 30. To release the device 10 from the catheter 450 a current is applied to the guidewire 465, which causes the joint 455 to sever from the proximal end 20 of the catheter 10. Further discussion of the construction of, placement of, and other physical details of such electrolytically severable joints may be found in U.S. Pat. No. 5,122,136 to Guglielmi et al.; U.S. Pat. No. 5,354,295 to Guglielmi et al.; and U.S. Pat. No. 5,624,449 to Pham et al; and others. It should be noted that other types of vaso-occlusive devices, such as vaso-occlusive device 110, can be delivered within the aneurysm 40 in the manner described immediately above.

Alternatively, referring to FIGS. 10(*a*)-(*c*), a retractable sheath method of delivering a vaso-occlusive device, and in this case vaso-occlusive device 310, to the aneurysm 40 is illustrated. Turning to FIG. 10(*a*), the catheter 550 is steered to just within the neck 70 of the aneurysm 40. At this point, the vaso-occlusive device 10 is in its undeployed shape, and is placed over an inner guidewire 565 that extends through the lumen 580 of the delivery catheter 565. The outer wall 555 of the catheter 565 that defines the lumen 580 functions as a sheath. The assembly of the vaso-occlusive device 310 and the guidewire 565 extends through the lumen 580 of the delivery catheter 450 such that the device 10 is positioned at the distal end of the catheter 550.

Turning to FIG. 10(*b*), the guidewire 565 is then pushed so that the distal end of vaso-occlusive device 310 extends out of the catheter 550, through the neck 70, and into the aneurysm 40. Once unconstrained from the catheter 550, the distal end 330 of the device 310 is allowed to expand into a first flattened disk adjacent the inner wall near the neck 70 within the aneurysm 40.

As described above, the device 310 may be configured to be in its martensite phase when delivered to the aneurysm 40 and expand upon exposure to the temperature of the aneurysm 40. Thus, when outside of the catheter 550, the temperature of the device 310 rises and the device 310 enters the austenite phase and expands into its deployed shape. Alternatively, the device 310 may be configured to be super-elastic and expand upon being unconstrained by the catheter 550.

Turning now to FIG. 10(*c*), the guidewire 565 continues to push the device 310 out of the catheter until the proximal end 320 of the device 310 is deployed just outside of the aneurysm 40, expanding into its deployed shape, e.g., a second flattened disk, as described above with the distal end 330. To release the device 310 from the catheter 450, the guidewire 565 is pulled out of the device 310 and the catheter 550 is pulled out of the aneurysm 40 and blood vessel 60. The expanded 310 device is secured in position within the aneurysm 40 and will not be pulled out with the catheter 550. It should be noted that other types of vaso-occlusive devices, such as vaso-occlusive device 310, can be delivered within the aneurysm 40 in the manner described immediately above.

As mentioned above, a vaso-occlusive device, such as vaso-occlusive device 310, may function as a vaso-occlusive device and/or function as a vaso-occlusive device retainer. In this regard, after deployment, finer vaso-occlusive devices 730 may be delivered into the aneurysm 40 to be retained by the device 310, as illustrated in FIG. 10(*d*). This is achieved by maintaining an axial lumen within a vaso-occlusive device to allow a catheter 740 to fit through and insert materials such as vaso-occlusive coils 730 or embolic liquids to further improve thrombogenecity within the aneurysm 700.

Figure 11A:
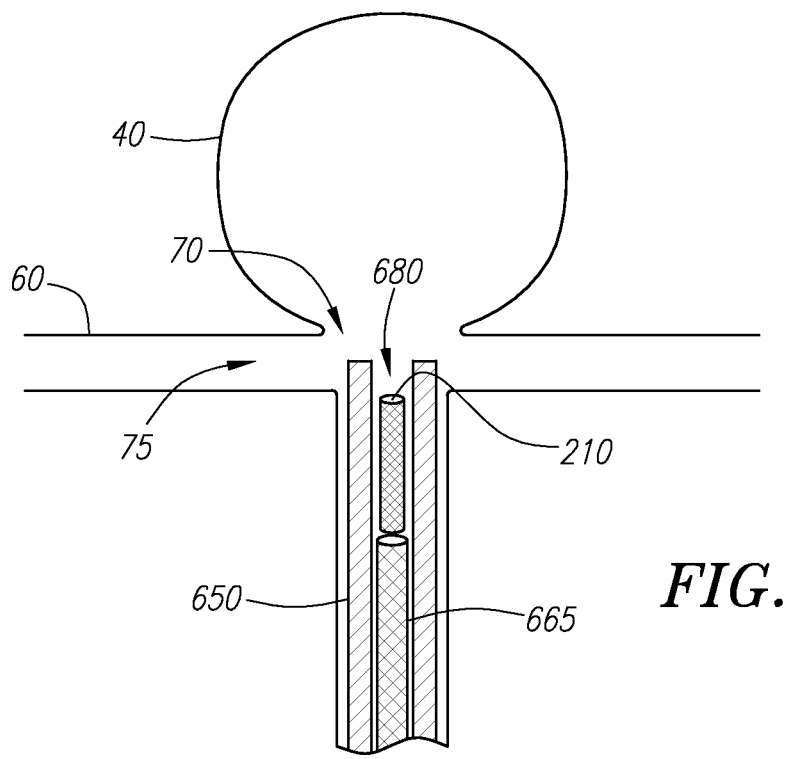
FIGS. 11(a)-(c) illustrate a preferred method of delivering and deploying the vaso-occlusive device of FIG. 5 into the aneurysm.
Figure 11B:
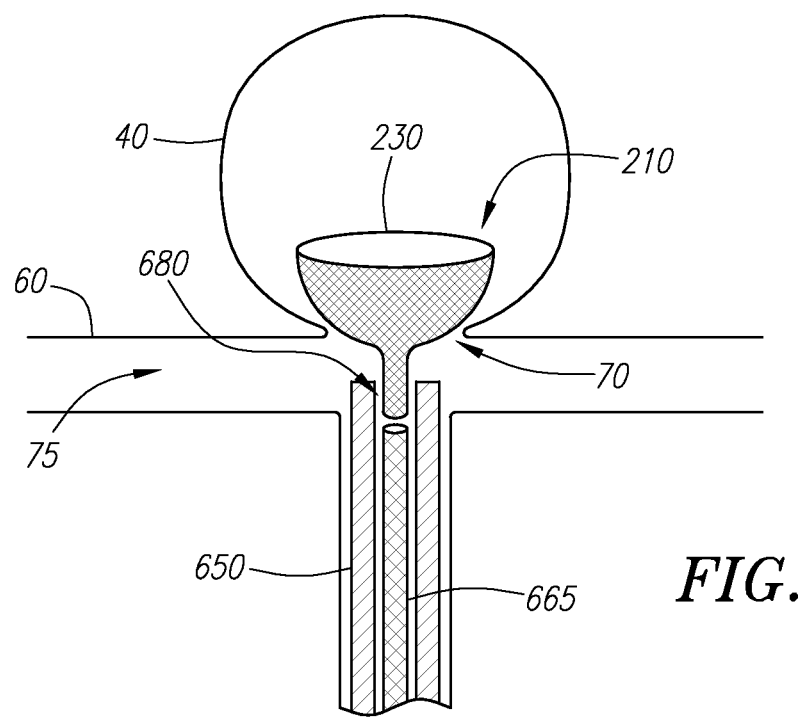
Figure 11C:
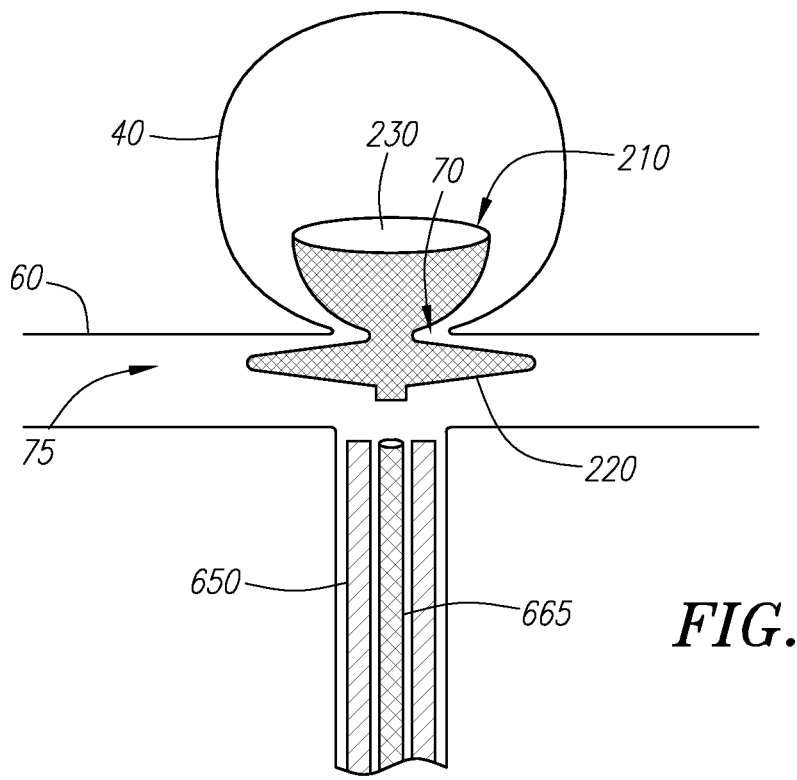

In another alternative, turning to FIGS. 11(*a*)-(*c*), a push method of delivering a vaso-occlusive device, and in this case vaso-occlusive device 210, to the aneurysm 40 is illustrated. Turning to FIG. 11(*a*), the catheter 650 is steered to just within the neck 70 of the aneurysm 40. At this point, the vaso-occlusive device 210 is in its undeployed shape, and is placed within the lumen 680 of a delivery catheter 650 near the distal tip of the catheter 650, which is steered to aneurysm 40, just outside of the neck 70. A guidewire 665, extending through the lumen 655 is positioned such that it is capable of pushing the device 210 out of the catheter 650 and into the aneurysm 40, where the device 230 may expand into its deployed shape, as described above.

Turning to FIG. 11(*b*), the guidewire 665 is then pushed so that the distal end of vaso-occlusive device 210 extends out of the catheter 650, through the neck 70, and into the aneurysm 40. Once unconstrained from the catheter 550, the distal end 230 of the device 210 is allowed to expand into a flared open cup shape adjacent the inner wall near the neck 70 within the aneurysm 40.

As described above, the device 210 may be configured to be in its martensite phase when delivered to the aneurysm 40 and expand upon exposure to the temperature of the aneurysm 40. Thus, when outside of the catheter 650, the temperature of the device 210 rises and the device 210 enters the austenite phase and expands into its deployed shape. Alternatively, the device 210 may be configured to be super-elastic and expand upon being unconstrained by the catheter 650.

Turning now to FIG. 11(*c*), the guidewire 665 continues to push the device 210 out of the catheter until the proximal end 220 of the device 210 is deployed just outside of the aneurysm 40, expanding into its deployed shape, e.g., a flattened disk, as described above with the distal end 230. The catheter 650 is then pulled out of the aneurysm 40 and blood vessel 60 to separate itself from the device 210. The expanded 210 device is secured in position within the aneurysm 40 and will not be pulled out with the catheter 650. It should be noted that other types of vaso-occlusive devices, such as vaso-occlusive device 210, can be delivered within the aneurysm 40 in the manner described immediately above.

While embodiments of the present invention have been shown and described, various modifications may be made without departing from the spirit and scope of the present invention, and all such modifications and equivalents are intended to be covered.

The invention claimed is:

1. A system for implanting a vaso-occlusive device in an aneurysm, the aneurysm having an aneurysmal neck and an aneurysmal inner wall, the system comprising:
   an elongate delivery member; and
   a vaso-occlusive device comprising a mesh-like structure detachably coupled to a distal end of the delivery member by a severable link, the mesh-like structure having a collapsed delivery configuration and an expanded deployed configuration, wherein in the expanded deployed configuration, the mesh-like structure comprises a proximal member, a distal member, and an elongated tubular element having a first end coupled to the proximal member and a second end coupled to the distal member,
   the mesh-like structure being configured to be inserted in its entirety through the aneurysmal neck when in the delivery configuration and attached to the delivery member, and to expand into the deployed configuration when detached from the delivery member and implanted within the aneurysm,
   wherein when the mesh-like structure is in the deployed configuration, detached from the delivery member and implanted within the aneurysm, the proximal and distal members comprise respective opposing concave inner surfaces separated by the elongated tubular element, and respective convex outer surfaces seated against respective proximal and distal portions of the aneurysmal inner wall.

2. The system of claim 1, wherein at least one of the proximal member and distal member is configured to expand by heat activation into the deployed configuration.

3. The system of claim 1, wherein at least one of the proximal member and distal member is configured to expand into the deployed configuration upon release of a compressive force.

4. The system of claim 1, wherein the mesh-like structure is formed from a plurality of braided fine wires.

5. The system of claim 4, wherein the fine wires have varying diameters.

6. The system of claim 4, wherein one or more of the fine wires are radiopaque.

7. The system of claim 1, wherein the mesh-like structure is composed of a NiTi alloy.

8. The system of claim 1, wherein the mesh-like structure is coated with radiopaque material.

9. The system of claim 1, further comprising radiopaque markers coupled to the mesh-like structure.

10. The system of claim 1, wherein the mesh-like structure is configured to allow another vaso-occlusive device to be delivered into the aneurysm, and to retain the other vaso-occlusive device within the aneurysm.

11. The system of claim 1, wherein the severable link is electrolytically severable.

12. The system of claim 1, wherein the severable link is mechanically severable.

* * * * *